United States Patent [19]
Peng

[11] Patent Number: 5,527,241
[45] Date of Patent: Jun. 18, 1996

[54] JOGGING EXERCISER

[76] Inventor: Yue-Hong Peng, No. 30-6, Chi-Chou, Chi-Chou Li, Chu-Pei City, Hsin-Chu Hsien, Taiwan

[21] Appl. No.: 521,909

[22] Filed: Aug. 31, 1995

[51] Int. Cl.6 .................................................. A63B 22/02
[52] U.S. Cl. .................................................. 482/54; 482/51
[58] Field of Search ................................. 482/52, 53, 54, 482/51, 148; 601/15, 19, 18, 20–22; 198/849, 848

[56] References Cited

U.S. PATENT DOCUMENTS

| | | | |
|---|---|---|---|
| 4,509,510 | 4/1985 | Hook | 482/54 |
| 4,925,183 | 5/1990 | Kim | 482/54 |
| 5,186,703 | 2/1993 | Huang | 482/148 |
| 5,382,222 | 1/1995 | Yih-Jong | 601/15 |
| 5,411,454 | 5/1995 | Chang | 482/148 |

*Primary Examiner*—Stephen R. Crow
*Attorney, Agent, or Firm*—Jason Z. Lin

[57] ABSTRACT

A jogging exerciser having a plurality of rollers and a plurality of beads mounted onto a belt having a sufficient width is disclosed. The beads are combined together by a string and then mounted onto the top surface of the belt. A pair of handles are provided perpendicularly at one end of the housing enclosing the rollers. The rotation of the rollers is controlled by a speed reducing motor.

4 Claims, 4 Drawing Sheets

5,527,241

JOGGING EXERCISER

FIELD OF THE INVENTION

The present invention relates to a jogging exerciser and in particular to an exerciser which employs rollers and gear train as a driving mechanism such that the rotation of the rollers is uni-directional. The external surface of the rollers is surrounded with a belt of sufficient width. The direction of rotation of the belt is the same direction of the rollers. A plurality of magnetic beads for massaging are provided on the belt. Thus, the exerciser provides the jogger on the exerciser with a massaging effect.

BACKGROUND OF THE INVENTION

Walking paths which provide good health for the joggers are built in parks and community center. The path is designed by arranging a plurality of circular or substantially rounded stones or fine rocks in an orderly fashion onto the surface of the walking path. When a person is walking on this path, due to the weight of the walker, the stones are in contact with the bare feet of the walker. According to experience and reports, it is said that the massaging effect can be obtained for a short distance of walking. If the walker spends too much time on the path, the uneven path surface will injure the bare feet. In turn, the other organs of the body of the walker may be thus hurt. As a result of the drawback, the jogger exerciser in accordance with the present invention will overcome the above drawbacks. Another advantage of the jogging exerciser of the present invention is that the exerciser can be used at any time of the day and at all environments.

SUMMARY OF THE INVENTION

It is an object of the present invention to provide a jogging exerciser wherein a belt of sufficient width surrounds a plurality of rollers which are driven by a speed reducing motor. The exerciser can thus be used in a limited space indoors.

It is another object of the present invention to provide a jogging exerciser having a belt of sufficient width mounted with a plurality of massaging beads which are moveable and are magnetic.

It is a further object of the present invention to provide a jogging exerciser of which the belt can be depressed due to the body weight of the jogger and the relative distance of the beads changed and thus the beads provide a massaging effect.

Other features and advantages of the present invention will become apparent during the course of the following description.

DETAILED DESCRIPTION OF THE PREFERRED EMBODIMENT

Figure 1:
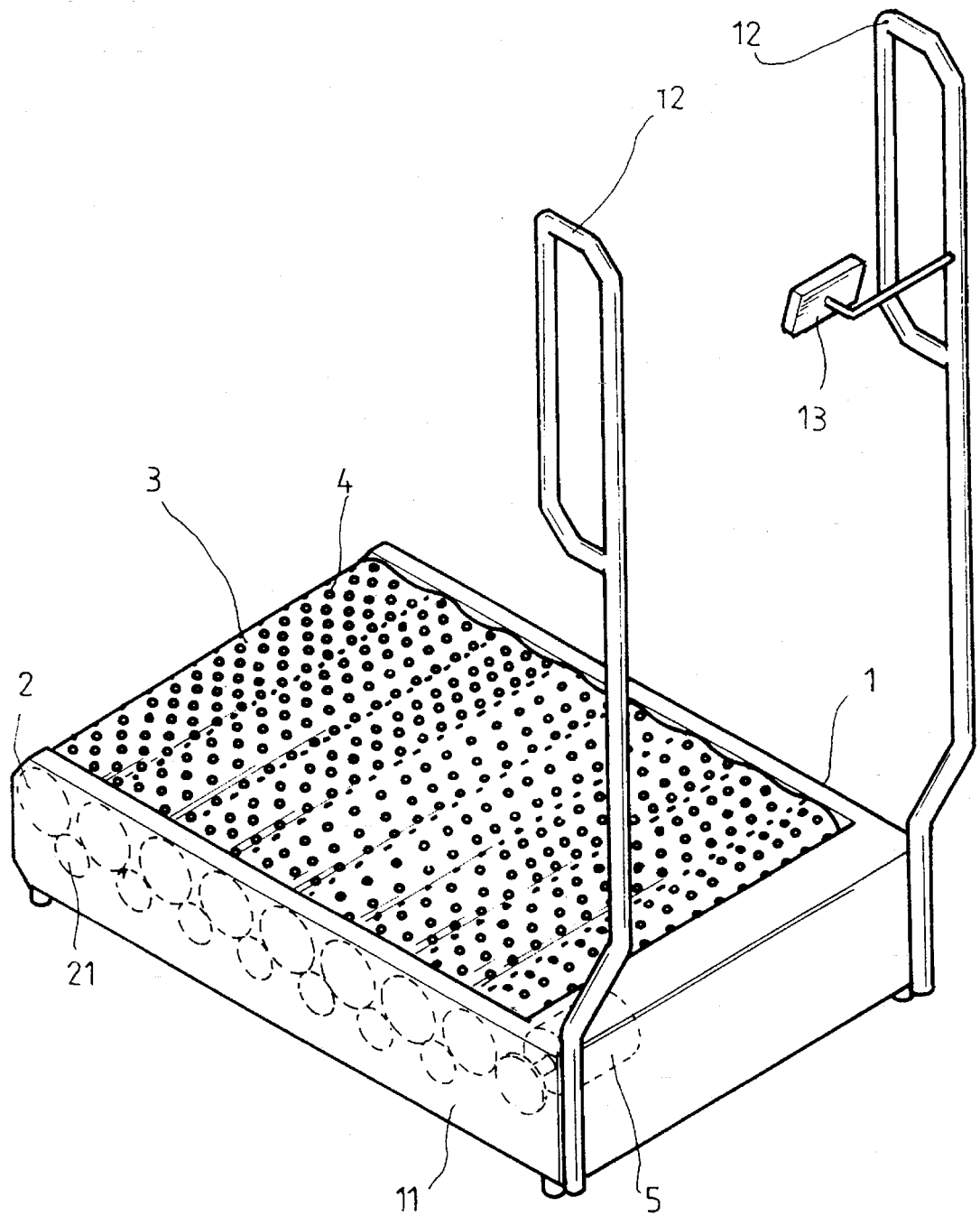
FIG. 1 is a perspective view showing a jogging exerciser in accordance with the present invention.

Referring to the drawings in detail wherein like numerals designate like parts and referring particularly to FIG. 1 which shows a jogging exerciser in accordance with the present invention, the jogging exerciser comprises a body 1 formed from a plastic material to define a housing 11, a speed reducing motor 5 mounted inside the housing 11 and a plurality of rollers including a first roller 2 directly driven by the motor 5. In between the rollers 2 and the bottom thereof, an auxiliary geared wheel 21 is provided and the wheel 21 is engaged with the rollers 2 such that the rollers 2 are all rotated in the same direction. The external surface of the rollers 2 is individually surrounded with a belt 3 having a sufficient width. A plurality of beads 4 are arranged horizontally on the surface of the belt 3. A pair of handles 12 are mounted perpendicularly at the front end of the body 1 for the holding of the jogger.

A controller 13 for the controlling of power, timing and speed adjustment is provided at the inner edge of one of the handles 12.

Figure 2:
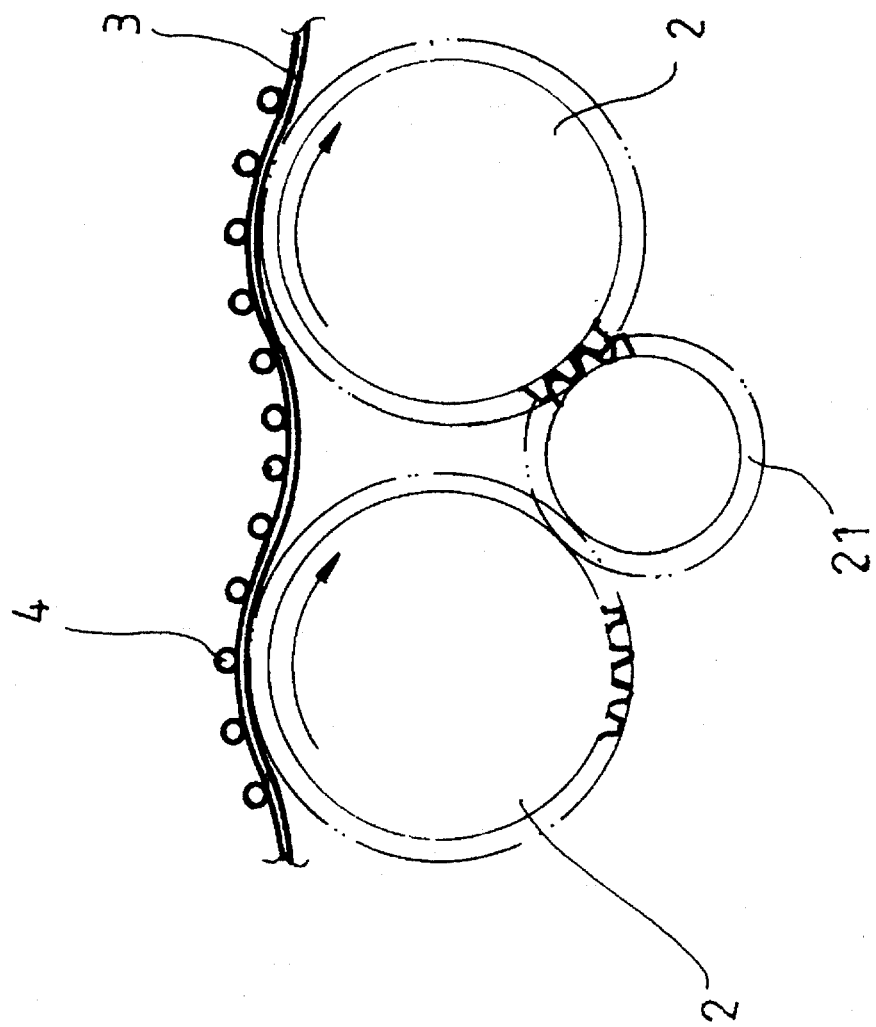
FIG. 2 is a schematic view of the driving mechanism of the jogging exerciser in accordance with the present invention.

Referring to FIG. 2, which shows the driving mechanism of the jogging exerciser in accordance with the present invention, the auxiliary geared wheel 21 is provided at the bottom of and in between the rollers 2. The auxiliary geared wheel 21 is engaged with the rollers 2 such that the geared wheel 21 causes the rollers 2 to rotate in the same direction. Thus, the belt 3 does not need a conveying belt to be driven. When the beads 4 on the belt 3 rotate at a position on the top end of the roller 2, the soles of the feet of the jogger is provided with a maximum massaging action by the beads 4. When the beads 4 move to a position in between the rollers 2, it has a minimum massaging effect.

In accordance with the present invention, the beads 4 are mounted in such a way that a horizontal space of about 2 cm and a vertical space of about 1 cm are provided between two successive beads 4 so as to provide the best massaging effect.

Figure 3:
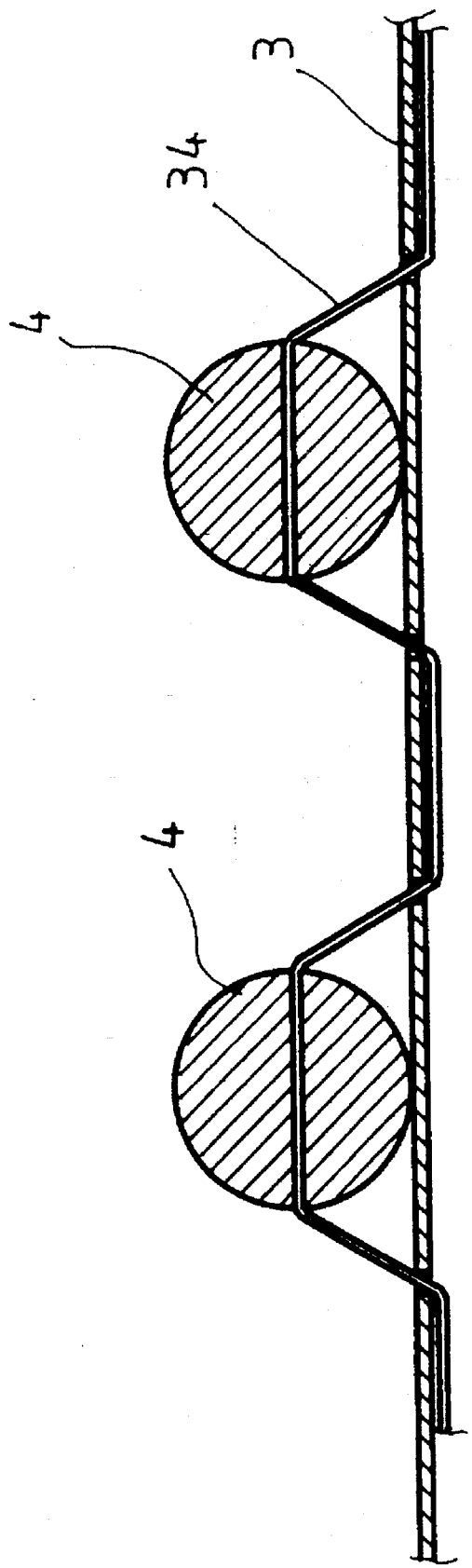
FIG. 3 is a sectional view of the combination of the massaging beads and the belt in accordance with the present invention.

Referring to FIG. 3, there is shown the sectional view of the massaging beads 4 in combination with the belt 3. The plurality of the beads 4 are mounted together by means of a string 34 via the core formed at the center of the beads 4. There is a space in between each rows of beads. The string 34 having a plurality of beads 4 thereon is mounted onto the belt 3 in such a way that the beads 4 are on the top surface of the belt 3 and the string 34 is tightened at the bottom of the belt 3. Due to the body weight of the jogger, a depression will be formed when the jogger steps onto the belt 3. At this instance, the beads 4 will produce a massaging effect on the soles of the feet of the jogger. The beads 4 on the string 34 can be replaced with that having varying size and distribution.

Figure 4:
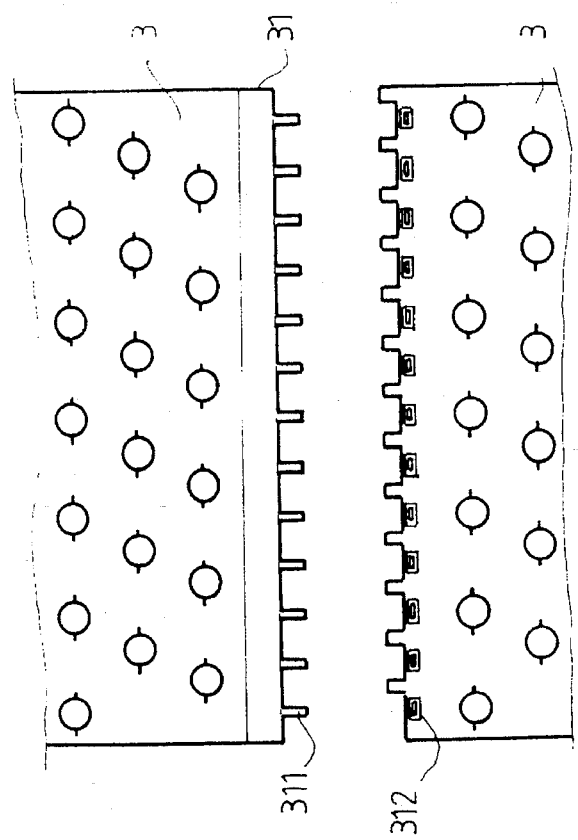
FIGS. 4 and 5 are schematic views of the belt of the jogging exerciser in accordance with the present invention.
Figure 5:
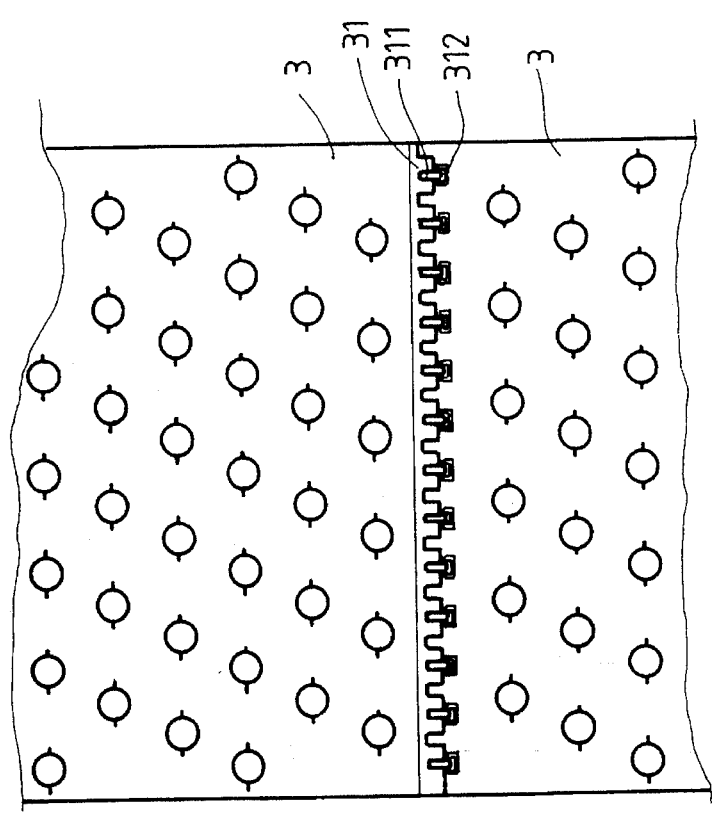

FIGS. 4 and 5 show the mounting of the belt 3. The belt 3 surrounds the rollers 2 and then connected at its ends 31 of which one end is provided with a plurality of protruded elements 311 and the other end is provided with a plurality of holes 312. The protruded elements 311 are inserted into the corresponding holes 312 and are then folded and securely mounted by adhesive. This has been clearly shown in FIG. 5.

It is to be understood that the forms of the invention herewith shown and described are to be taken as preferred examples of the same and that various changes in the shape, size and arrangement of parts may be resorted to, without departing the spirit of the invention or scope of the accompanying claims.

What is claimed is:

1. A jogging exerciser comprising a body defining a housing and a plurality of rollers rotatably mounted inside the housing and further comprising a speed reducing motor mounted within the housing to directly drive a first one of the rollers, the first roller being engaged to an auxiliary geared wheel which is individually mounted in between the rollers such that the rotation of the rollers is in a same direction, a belt of a pre-determined width having a plurality of magnetic beads for massaging distributed thereon, the belt surrounding the external surface of the rollers, and a pair of handles mounted perpendicularly at one end of the housing.

2. The jogging exerciser as claimed in claim 1, wherein a controller for controlling speed is mounted at one of the handles.

3. The jogging exerciser as claimed in claim 1, wherein the beads are connected by a string.

4. The jogging exerciser as claimed in claim 1, wherein the beads are mounted on the surface of the belt.

* * * * *